United States Patent [19]

Schmetzer et al.

[11] Patent Number: 4,599,348

[45] Date of Patent: Jul. 8, 1986

[54] 1-AZOLYL-SUBSTITUTED OXIME ETHER FUNGICIDES

[75] Inventors: Johannes Schmetzer, Pulheim; Jörg Stetter, Wuppertal; Paul Reinecke; Gerd Hänssler, both of Leverkusen, all of Fed. Rep. of Germany

[73] Assignee: Bayer Aktiengesellschaft, Leverkusen, Fed. Rep. of Germany

[21] Appl. No.: 648,910

[22] Filed: Sep. 7, 1984

[30] Foreign Application Priority Data

Sep. 22, 1983 [DE] Fed. Rep. of Germany ....... 3334220

[51] Int. Cl.[4] .................. A01N 43/653; C07D 249/08

[52] U.S. Cl. .................................... 514/383; 514/359; 514/364; 514/374; 514/378; 514/397; 514/399; 548/101; 548/131; 548/143; 548/235; 548/247; 548/255; 548/262; 548/336; 548/341

[58] Field of Search ............... 548/341, 336, 255, 235, 548/247, 131, 143, 262, 101; 514/397, 399, 383, 378, 374, 359, 364

[56] References Cited

U.S. PATENT DOCUMENTS

| | | | |
|---|---|---|---|
| 4,347,372 | 8/1982 | Föry et al. | 548/341 X |
| 4,360,526 | 11/1982 | Zeeh et al. | 548/341 X |

FOREIGN PATENT DOCUMENTS

| | | | |
|---|---|---|---|
| 0004917 | 10/1979 | European Pat. Off. | 548/262 |
| 0018943 | 11/1980 | European Pat. Off. | 548/341 |
| 0038972 | 11/1981 | European Pat. Off. | 548/262 |
| 0095677 | 12/1983 | European Pat. Off. | 548/262 |
| 2657578 | 12/1976 | Fed. Rep. of Germany | 548/341 |
| 2723942 | 5/1977 | Fed. Rep. of Germany | 548/341 |
| 2816817 | 4/1978 | Fed. Rep. of Germany | 548/341 |
| 3005899 | 9/1981 | Fed. Rep. of Germany | 548/341 |
| 3150984 | 6/1983 | Fed. Rep. of Germany | 548/262 |

OTHER PUBLICATIONS

*Chemical Abstracts*, 95:204008e (1981) [Ger. Offen. 3,005,899, Ertel, et al., 9/3/81].

*Primary Examiner*—Richard A. Schwartz
*Attorney, Agent, or Firm*—Sprung Horn Kramer & Woods

[57] ABSTRACT

Combating fungi with novel 1-azolyl-substituted oxime ethers of the formula

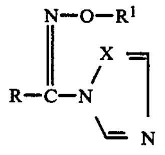

in which R is alkyl, alkoxyalkyl, alkenyl, alkinyl or cycloalkyl; or aralkyl, phenoxyalkyl or phenyl optionally substituted in the aromatic part, $R^1$ is alkyl, alkenyl, alkinyl, or optionally substituted aralkyl or heteroalkyl, and X is nitrogen or the CH group, or physiologically acceptable addition products thereof with acids or metal salts.

10 Claims, No Drawings

1-AZOLYL-SUBSTITUTED OXIME ETHER FUNGICIDES

The present invention relates to new 1-azolyl-substituted oxime ethers, a process for their preparation and their use as fungicides.

1-Methylazolyl-substituted oxime ethers with a fungicidal action have already been disclosed (in this context, DE-OS (German Published Specification) No. 2,816,817. DE-OS (German Published Specification) No. 2,723,942 and DE-OS (German Published Specification) No. 2,657,578).

However, the action of the known compounds is not always completely satisfactory, especially when low amounts are applied.

The new 1-azolyl-substituted oxime ethers of the general formula

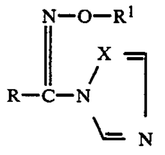
(I)

in which

R represents alkyl, alkoxyalkyl, alkenyl, alkinyl, cycloalkyl, aralkyl, phenoxyalkyl or phenyl, it being possible for the last three radicals mentioned to be substituted in the aromatic part, $R^1$ represents alkyl, alkenyl, alkinyl, optionally substituted aralkyl or heteroaralkyl and X represents nitrogen or the CH group, and physiologically acceptable acid addition salts and metal salt complexes thereof, have now been found.

The 1-azolyl-substituted oxime ethers of the formula (I) are obtained when oximes of the general formula

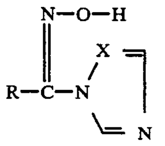
(II)

in which

R and X have the abovementioned meaning, are reacted with alkyl, alkenyl or alkinyl halides of the general formula $$Hal—R^1 \quad (III)$$

in which $R^1$ has the abovementioned meaning and

Hal represents chlorine or bromine, if appropriate in the presence of a solvent and an acid-binding agent.

The compounds of the general formula (I) according to the invention have powerful fungicidal properties. Surprisingly, the 1-azolyl-substituted oxime ethers according to the invention exhibit a substantially more powerful fungicidal action than the 1-methylazolyl-substituted oxime ethers known from the prior art. The new compounds are thus an enrichment of the art.

The above formula (I) provides a general definition of the 1-azolyl-substituted oxime ethers according to the invention. Preferred compounds of the formula (I) are those in which R represents straight-chain or branched alkyl with 1 to 12 carbon atoms, alkoxyalkyl with 1 to 4 carbon atoms in each alkyl part, alkenyl or alkinyl with in each case 2 to 5 carbon atoms or cycloalkyl with up to 6 carbon atoms in the ring, or furthermore aralkyl with 1 to 4 carbon atoms in the alkyl part and 6 to 10 carbon atoms in the aryl part, it being possible for the aryl part to be optionally substituted by halogen or by alkyl and/or alkoxy groups with in each case up to 4 carbon atoms, or, finally, phenoxyalkyl with up to 3 carbon atoms in the straight-chain or branched alkyl part or phenyl, it being possible for the last two radicals mentioned to be substituted on the phenyl by halogen or alkyl and/or alkoxy groups with in each case 1 to 4 carbon atoms, $R^1$ represents alkyl with 1 to 6 carbon atoms or alkenyl or alkinyl with in each case 3 to 5 carbon atoms, aralkyl with 1 to 3 carbon atoms in the alkyl part and 6 to 10 carbon atoms in the aryl part, it being possible for the latter to be substituted by halogen or alkyl and/or alkoxy with in each case up to 4 carbon atoms, or represents heteroaralkyl with 1 or 2 carbon atoms in the alkyl part and a 5-membered aromatic heteroring with 1 to 3 nitrogen atoms and, if appropriate, an oxygen atom in the heteroaryl part, and X has the meaning given in the definition of the invention.

Particularly preferred compounds of the formula (I) are those in which

R represents tert.-butyl, alkoxyalkyl with 1 to 3 carbon atoms in each alkyl part or phenoxyalkyl with up to 3 carbon atoms in the alkyl part, it being possible for the phenyl part to be mono-, di- or tri-substituted by fluorine, chlorine, bromine, methyl and/or methoxy, $R^1$ represents methyl, ethyl, propyl, butyl, allyl or propargyl, or benzyl, which can be mono-, di- or tri-substituted in the phenyl part by halogen, methyl and methoxy, or triazolylmethyl or imidazolylmethyl, and X has the meaning given in the definition of the invention.

The following compounds of the general formula

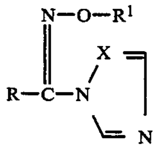
(I)

may be mentioned specifically, in addition to the preparation examples:

| R | $R^1$ | X |
|---|---|---|
| 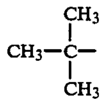 | $CH_3$ | CH |
| " | $C_2H_5$ | " |
| " | $CH_2—CH=CH_2$ | " |

-continued
| R | $R^1$ | X |
|---|---|---|
| " | $CH_2—C≡CH$ | " |
| " | 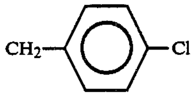 | " |
| " | 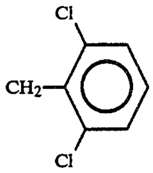 | " |
| " | 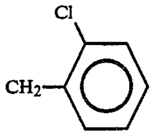 | " |
| " | 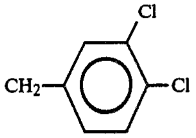 | " |
| " | 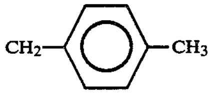 | " |
| " | 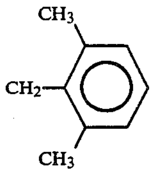 | " |
| " | 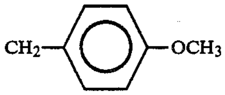 | " |
| " | 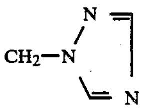 | " |
| " | $CH_3$ | N |
| " | $C_2H_5$ | " |
| " | $CH_2—CH=CH_2$ | " |
| " | $CH_2—C≡CH$ | " |
| " | 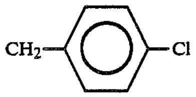 | " |
| " | 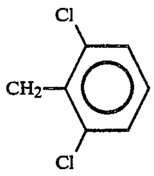 | " |
-continued
| R | $R^1$ | X |
|---|---|---|
| " | 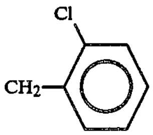 | " |
| " | 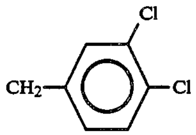 | " |
| " | 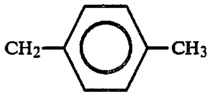 | " |
| " | 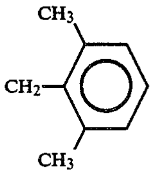 | " |
| " | 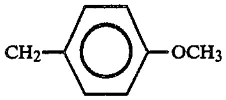 | " |
| " | 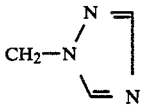 | " |
| 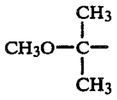 | $CH_3$ | CH |
| " | $C_2H_5$ | " |
| " | $CH_2—CH=CH_2$ | " |
| " | $CH_2—C≡CH$ | " |
| " | 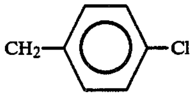 | " |
| " | 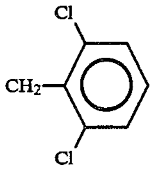 | " |
| " | 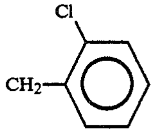 | " |
| " | 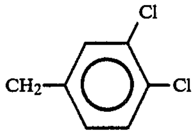 | " |

-continued
| R | $R^1$ | X |
| --- | --- | --- |
| " | 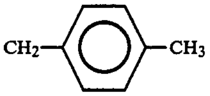 | " |
| " | 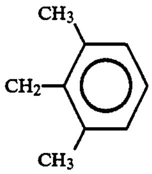 | " |
| " | 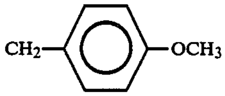 | " |
| " | 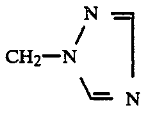 | " |
| 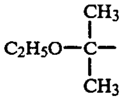 | $CH_3$ | " |
| " | $C_2H_5$ | " |
| " | $CH_2-CH=CH_2$ | " |
| " | $CH_2-C\equiv CH$ | " |
| " | 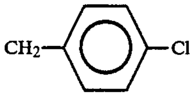 | " |
| " | 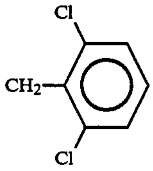 | " |
| " | 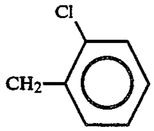 | " |
| " | 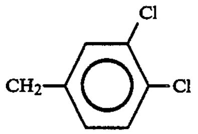 | " |
| " | 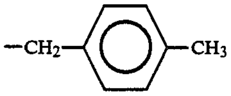 | " |
| " | 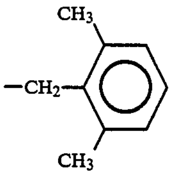 | " |
-continued
| R | $R^1$ | X |
| --- | --- | --- |
| " | 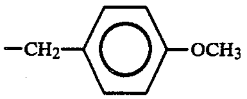 | " |
| " | 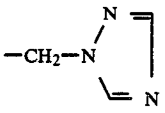 | " |
| 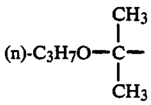 or (iso) | $CH_3$ | " |
| " | $C_2H_5$ | " |
| " | $-CH_2-CH=CH_2$ | " |
| " | $-CH_2-C\equiv CH$ | " |
| " | 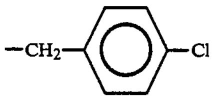 | " |
| " | 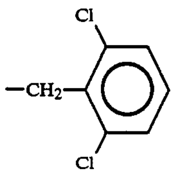 | " |
| " | 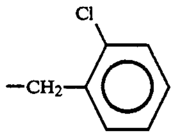 | " |
| " | 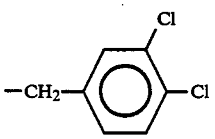 | " |
| " | 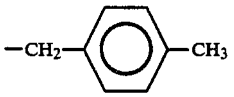 | " |
| " | 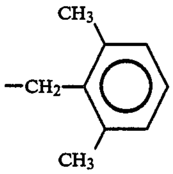 | " |
| " | 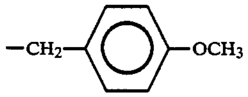 | " |
| " | 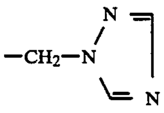 | " |

-continued

| R | $R^1$ | X |
|---|---|---|
| 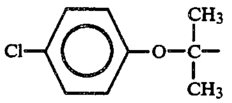 | $CH_3$ | " |
| " | $C_2H_5$ | " |
| " | $-CH_2-CH=CH_2$ | " |
| " | $-CH_2-C\equiv CH$ | " |
| " | 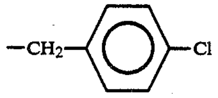 | " |
| " | 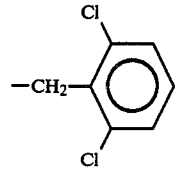 | " |
| " | 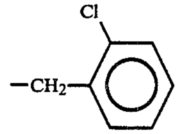 | " |
| " | 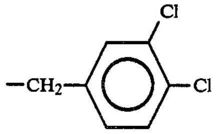 | " |
| " | 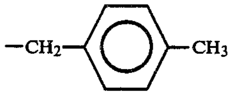 | " |
| " | 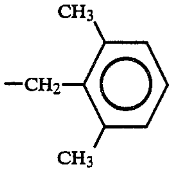 | " |
| " | 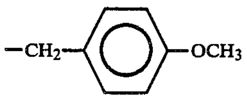 | " |
| " | 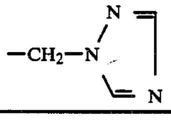 | " |

If, for example, 2,2-dimethyl-1-oximino-1-(N-imidazolyl)-propane and p-chlorobenzyl chloride are used as starting substances for the preparation of the compounds of the formula (I) according to the invention, the course of the reaction can be represented by the following equation:

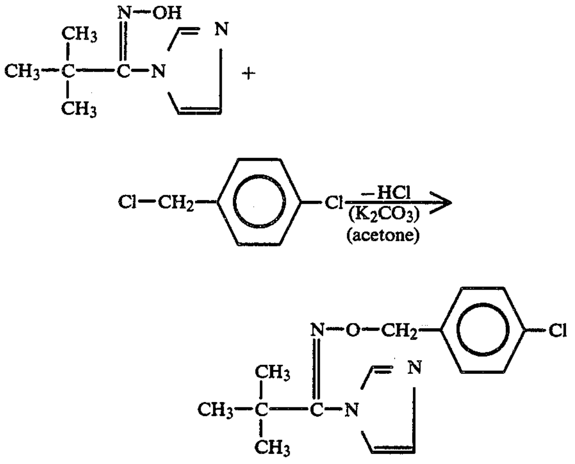

The general formula (II) provides a definition of the oximes to be used according to the invention as starting substances. In this formula, R and X have the abovementioned preferred meanings. Some of the compounds are already known (in this context, compare the statements in DE-OS (German Published Specification) No. 2,613,167. They can be prepared, for example, by reacting hydroxamic acid halides of the formula

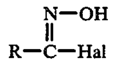 (IV)

in which

R has the abovementioned meaning and

Hal represents chlorine or bromine, with azoles of the formula

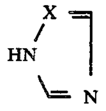 (V)

in which

X has the abovementioned meaning, in suitable organic solvents, such as, for example, in ethers, such as tetrahydrofuran or dioxane, in the presence of an acid-binding agent, such as, for example, triethylamine, in the temperature range between 0° and 30° C. 1 to 2 mols of azole (V) and 1 mol of an acid-binding agent are thereby advantageously employed per mol of the compound of the formula (IV). The oximes of the formula (II) are isolated in the customary manner by stripping off the solvent and precipitating the product by dilution with water.

The hydroxamic acid halides of the formula (IV) used as intermediates are known (compare H. Ulrich "The Chemistry of Imidoyl Halides", pages 157-172, Plenum Press, New York (1968) and the literature references quoted therein). Compounds which are not yet known can easily be prepared by the processes described therein, thus, for example, by chlorination of the corresponding aldoximes in inert solvents at low temperatures, for example at −30° to 0° C.

New hydroxamic acid halides of the general formula

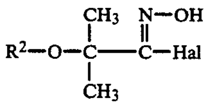

(Iva)

in which $R^2$ represents alkyl or optionally substituted phenyl and

Hal represents chlorine or bromine, can be prepared by reacting halogeno-hydroxamic acid halides of the formula

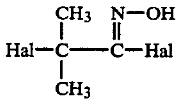

(VI)

in which

Hal represents chlorine or bromine, with hydroxy compounds of the formula $R^2$—OH (VII)

in which $R^2$ has the abovementioned meaning, in a manner which is known in principle ("Williamson's Ether Synthesis"). Weakly basic substances, such as calcium carbonate, are used here to bind the hydrogen halide acid liberated (in this context, compare the statements in J. prakt. Chemie 311, pages 775–785 (1969). The solvent used can be either the hydroxy compound, employed in excess, or acetonitrile. The reaction is carried out in the temoerature range between +50° and 100° C. Up to 10 mols of the hydroxy compound of the formula (VII) and 1 to 2 mols of calcium carbonate are thereby employed per mol of the dihalogen compound of the formula (VI). To isolate the compounds of the formula (Iva), the solvent is distilled off and the residue is extracted with ether.

The compounds of the general formula (VI) are obtained by reacting 2 mols of nitrosyl chloride with 1 mol of isobutylene at temperatures below 0° C. in ether saturated with hydrogen chloride. (J. prakt. Chemie 311, pages 775–785 (1969).

The general formula (III) provides a definition of the alkyl, alkenyl or alkinyl halides further required as starting substances for carrying out the reaction according to the invention. In this formula, $R^1$ has the abovementioned preferred meanings. The compounds are generally known. Heteroaralkyl halides can be obtained, for example, by reacting the corresponding hydroxy compounds with thionyl halides (Beilstein H26, E III/IV, page 46). The hydroxy compounds required can be obtained, for example, by adding formaldehyde onto an azole, such as, for example, 1,2,4-triazole (Beilstein H26, E III/IV, page 326).

Possible diluents for carrying out the process according to the invention for the preparation of the 1-azolyl-substituted oxime ethers of the formula (I) are polar organic solvents. These include, preferably, ketones, such as methyl ethyl ketone or acetone, and furthermore nitriles, such as acetonitrile, ethers, such as dioxane, and alcohols, such as methanol or ethanol.

All the customary acid-binding agents can be used as the acid-binding agents for carrying out the process according to the invention. These include, preferably, carbonates, such as sodium carbonate, potassium carbonate and sodium bicarbonate, and furthermore alcoholates, such as sodium methylate and sodium ethylate, and lower tertiary amines, such as triethylamine.

The reaction temperatures can be varied within a substantial range in carrying out the process according to the invention. In general, the reaction is carried out between 50° and 150° C., preferably at the boiling point of the solvent used.

In carrying out the process according to the invention, 1 to 2 mols of the compound (III) and 1 to 2 mols of acid-binding agent are preferably used per mol of the compound (II).

To isolate the compound (I), the solvent is distilled off, the residue is taken up in chloroform and the mixture is washed with sodium hydroxide solution. The concentrated organic phase is usually freed from residual solvent under a high vacuum.

The compounds of the formula (I) obtainable by the processes according to the invention can be converted into acid addition salts or metal salt complexes.

The following acids can preferably be used for the preparation of physiologically acceptable acid addition salts of the compounds of the formula (I): the hydrogen halide acids, such as, for example, hydrochloric acid and hydrobromic acid, in particular hydrochloric acid, and furthermore phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

The acid addition salts of the tompounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel. Possible anions of the salts are those which, preferably, are derived from the following acids: hydrogen halide acids, such as, for example, hydrochloric acid and hydrobromic acid, and furthermore phosphoric acid, nitric acid and sulphuric acid.

The metal salt complexes of the compounds of the formula (I) can be obtained in a simple manner by customary processes, thus, for example, by dissolving the metal salt in alcohol, for example ethanol, and adding the solution to the compound of the formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

The active compounds according to the invention are distinguished, in particular, by a good fungicidal action against powdery mildew, rust, Septoria and Pyrenophora teres on cereals and against apple scab. The active compounds are also effective against diseases in rice plantations.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, oorn cobs and tobacco stalks. As emulsifying and/or foam-forming agents there are suitabLe: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and as mixtures with fertilizers and other growth regulators.

The active compounds can be used as such, or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method, or to inject the active compound formulation or the active compound itself into the soil. The seed of the plants may also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%. are required at the place of action.

PREPARATION EXAMPLES

EXAMPLE 1

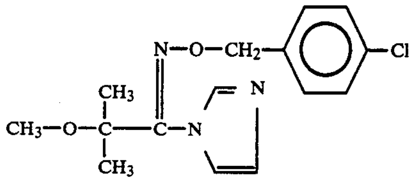

A mixture of 4.5 g (0.026 mol) of 2,2-dimethyl-2-methoxy-1-(imidazol-1-yl)-1-oximino-ethane, 4.8 g (0.03 mol) of p-chlorobenzyl chloride, 3.6 g (0.026 mol) of finely ground potassium carbonate and 50 ml of acetone is heated at the boiling point for 24 hours, while cooling under reflux. The mixture is then filtered with suction, the solvent is substantially stripped off from the filtrate and the residue is taken up in chloroform. The chloroform phase is washed twice with dilute sodium hydroxide solution, dried over sodium sulphate and freed from the solvent, finally under a pressure of 0.15 mbar and at a heating bath temperature of 100° C. 4.8 g of a viscous oil of refractive index $N_D^{20}$ 1.5589 are obtained, that is to say 58% of theory. Intermediate:

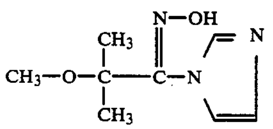

A solution of 9.9 g (0.066 mol) of 2,2-dimethyl-2-methoxy-1-chloro-1-oximino-ethane is very slowly added dropwise to a mixture of 9.0 g (0.132 mol) of imidazole and 6.7 g (0.066 mol) of triethylamine in 50 ml of absolute tetrahydrofuran at 0° C., with stirring. The mixture is allowed to come to room temperature and is subsequently stirred for 10 hours. The reaction batch is filtered, the filtrate is concentrated and the concentrate is diluted with water. The product which has precipitated is filtered off with suction, washed with petroleum ether and dried. 10.3 g of 2,2-dimethyl-2-methoxy-1-(imidazol-1-yl)-1-oximino-ethane of melting point 155°-160° C. are obtained, that is to say 85% of theory. Intermediate:

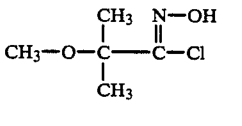

A mixture of 50 g (0.32 mol) of 2-methyl-1,2-dichloro-1-oximino-propane, 50 g (0.5 mol) of finely powdered calcium carbonate and 500 ml of absolute methanol is heated at the boiling point for 30 minutes, while cooling under reflux. The mixture is filtered, the filtrate is concentrated and the residue is extracted several times with ether. The ether phase is dried over sodium sulphate and filtered and the filtrate is concentrated. 38.4 g of 2,2-dimethyl-2-methoxy-1-chloro-1-oximino-ethane are obtained in the form of white crystals of melting point 95° C., and the yield is 79% of theory:

EXAMPLE 2

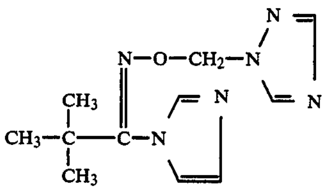

4.6 g (0.029 mol) of chloro-(1,2,4-triazol-1-yl)-methane hydrochloride are slowly added to a solution of 3.2 g (0.059 mol) of sodium methylate in methanol. After the solution has become clear, 5.0 g (0.029 mol) of 2,2-dimethyl-1-oximino-1-(imidazol-1-yl)-propane are also added. The mixture is subsequently stirred at room temperature for 10 hours and concentrated and the residue is taken up in very dilute sodium carbonate solution. The aqueous phase is extracted several times with chloroform and the extracts are dried over sodium sulphate and then freed from the solvent. 3.2 g of 2,2-dimethyl-1-(1,2,4,-triazol-1-yl-methyloximino)-1-(imidazol-1-yl)-propane as a viscous oil of refractive index $N_D^{20}$ 1.5152. The yield is 45% of theory.

The following compounds of the general formula

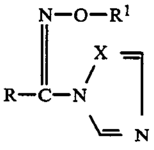

(I)

can be prepared in a corresponding manner:

| Example No. | R | $R^1$ | X | Melting point (°C.) or $N_D^{20}$ |
|---|---|---|---|---|
| 3 | 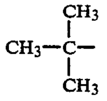 | 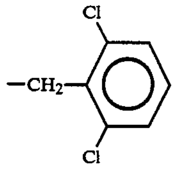 | N | 66 |
| 4 | ″ | 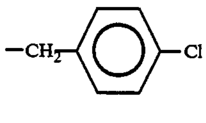 | CH | 1.5465 |
| 5 | ″ | 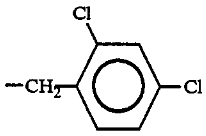 | CH | 1.5692 |
| 6 | 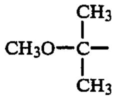 | 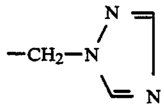 | CH | 1.5130 |

-continued

| Example No. | R | $R^1$ | X | Melting point (°C.) or $N_D^{20}$ |
|---|---|---|---|---|
| 7 | " | 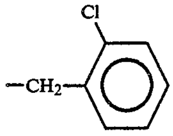 | CH | 1.5671 |
| 8 | " | 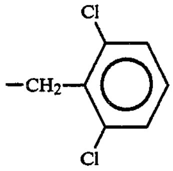 | CH | 1.5775 |
| 9 | 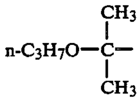 | 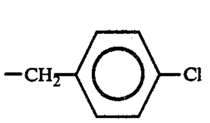 | CH | 1.5450 |
| 10 | 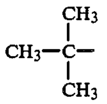 | 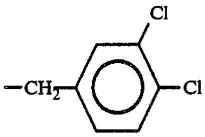 | N | 58 |
| 11 | 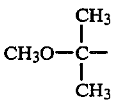 | 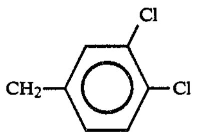 | CH | 1.5620 |
| 12 | 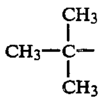 | $CH_3$ | CH | 1.4887 |
| 13 | " | 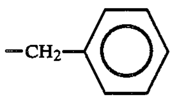 | N | 1.5237 |
| 14 | " | 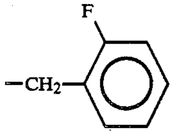 | N | 1.5168 |
| 15 | " | 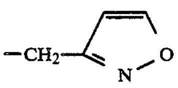 | N | 1.4997 |
| 16 | " | $-CH_2-CH=CH_2$ | N | 1.4820 |
| 17 | " | $-CH_2-C\equiv CH$ | N | 60-62 |
| 18 | " | 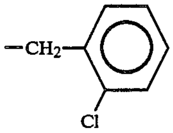 | N | 1.5334 |

EXAMPLE A

*Cochliobolus sativus* test (barley)/protective

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sorayed with a conidia suspension of *Cochliobolus sativus.* The plants remain in an incubation cabinet for 48 hours at 20° C. and 100% relative atmospheric humidity The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds according to the following preparation examples: 1, 9 and 11.

EXAMPLE B:

*Drechslerai graminea* test (barley)/seed treatment (syn. *Helminthosporium gramineum*)

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

The seed is embedded in sieved, moist standard soil and is exposed to a temperature of 4° C. in closed Petri dishes in a refrigerator for 10 days. Germination of the barley, and possibly also of the fungus spores, is thereby initiated. 2 batches of 50 grains of the pregerminated barley are subsequently sown 3 cm deep in standard soil and are cultivated in a greenhouse at a temperature of about 18° C., in seedboxes which are exposed to light for 15 hours daily.

About 3 weeks after sowing, the plants are evaluated for symptoms of stripe disease.

In this test, a clearly superior activity compared with the prior art is shown, for example, by the compounds according to the following preparation examples: 1.

EXAMPLE C:

Pyricularia test (rice)/protective

Solvent: 12.5 parts by weight of acetone

Emulsifier: 0.3 part by weight of alkylaryl polyglycol ether

To produce a suitable preparation of active compound, 1 part by weight of active compound is mixed with the stated amounts of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae.* The plants are then placed in a greenhouse at 100% relative atmosoheric humidity and 25° C.

Evaluation of the disease infestation is carried out 4 days after the inoculation.

In this test, a clearly superior activity compared with the prior art is shown, for example, by the compounds according to the following preparation examples: 1, 3, 4, 5, 7 and 9.

EXAMPLE D:

Pyricularia test (rice)/systemic

Solvent: 12.5 parts by weight of acetone

Emulsifier: 0.3 part by weight of alkylaryl polyglycol ether

To produce a suitable preparation of active compound, 1 part by weight of active compound is mixed with the stated amounts of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae.* Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples: 1, 3, 10, 4, 7 and 9.

EXAMPLE E:

Pellicularia test (rice)

Solvent: 12.5 parts by weight of acetone

Emulsifier: 0.3 part by weight of alkylaryl polyglycol ether

To produce a suitable preparation of active comoound, 1 part by weight of active compound is mixed with the stated amount of solvent, and the concentrate is diluted with water and the stated amount of emulsifier, to the desired concentration.

To test for activity, young rice plants in the 3 to 4 leaf stage are sprayed until dripping wet. The plants remain in a greenhouse until they have dried off. The plants are then inoculated with *Pellicularia sasakii* and are placed at 25° C. and 100% relative atmospheric humidity.

The evaluation of the disease infestation is carried out 5 to 8 days after the inoculation.

In this test, a clearly superior activity compared with the prior art is shown, for example, by the compounds according to the following preparation examples: 1, 3, 4, 6 and 9.

It is understood that the specification and examples are illustrative but not limitative of the present invention and that other embodiments within the spirit and scope of the invention will suggest themselves to those skilled in the art.

We claim:

1. A 1-axolyl-substituted oxime ether of the formula

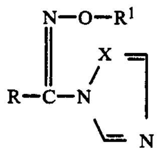

in which

R is alkyl with 1 to 12 carbon atoms; alkoxyalkyl with 1 to 4 carbon atoms in each alkyl part; alkenyl or alkinyl with in each case 2 to 5 carbon atoms; cycloalkyl with up to 6 carbon atoms in the ring; aralkyl with 1 to 4 carbon atoms in the alkyl part, the aryl part containing 6 to 10 carbon atoms and being optionally substituted by halogen or by alkyl and/or alkoxy groups with in each case up to 4 carbon atoms; or phenyl or phenoxyalkyl with up to 3 carbon atoms in the alkyl part, the phenyl being optionally substituted by halogen or alkyl and/or alkoxy groups with in each case 1 to 4 carbon atoms, $R^1$ is aralkyl with 1 to 3 carbon atoms in the alkyl part, the aryl part containing 6 to 10 carbon atoms and being optionally substituted by halogen or alkyl and/or alkoxy with in each case up to 4 carbon atoms; or heteroaralkyl with 1 or 2 carbon atoms in the alkyl part and a 5-membered aromatic hetero- ring with 1 to 3 nitrogen atoms and optionally an oxygen atom in the heteroaryl part, and X is nitrogen or the CH group, or a physiologically acceptable addition product thereof with an acid or metal salt.

2. A compound or addition product according to claim 1, in which

R is tert.-butyl, alkoxyalkyl with 1 to 3 carbon atoms in each alkyl part or phenoxyalkyl with up to 3 carbon atoms in the alkyl part, it being possible for the phenyl part to be mono-, di- or tri-substituted by fluorine, chlorine, bromine, methyl and/or methoxy, and $R^1$ is triazolylmethyl, imidazolylmethyl, or benzyl which is optionally mono- di- or tri-substituted in the phenyl part by halogen, methyl and/or methoxy.

3. A compound according to claim 1 wherein such compound is 2,2-dimethyl-2-methoxy-1-(4chlorobenzyloximino)-1-(imidazol-1-yl)-ethane of the formula

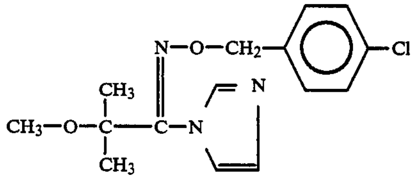

or a physiologically acceptable addition product thereof with an acid or metal salt.

4. A compound according to claim 1, wherein such compound is 2,2-dimethyl-1-(2,6-dichlorobenzyloximino)-1-(1,2,4-triazol-1-yl)-propane of the formula

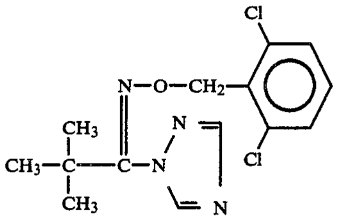

or a physiologically acceptable addition product thereof with an acid or metal salt.

5. A compound according to claim 1, wherein such compound is 2,2-dimethyl-1-(4-chlorobenzyloximino)-1-(imidazol-1-yl)-propane of the formula

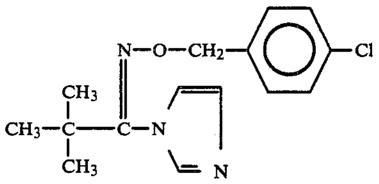

or a physiologically acceptable addition product thereof with an acid or metal salt.

6. A compound according to claim 1, wherein such compound is 2,2-dimethyl-2-methoxy-1-(2-chlorobenzyloximino)-1-(imidazol-1-yl)-ethane of the formula

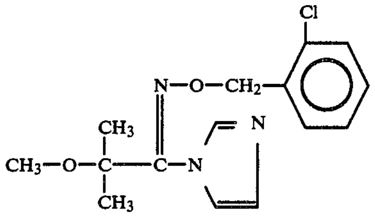

or a physiologically acceptable addition product thereof with an acid or metal salt.

7. A compound according to claim 1, wherein such compound is 2,2-dimethyl-1-(3,4-dichlorobenzyloximino)-1-(1,2,4-triazol-1-yl)-propane of the formula

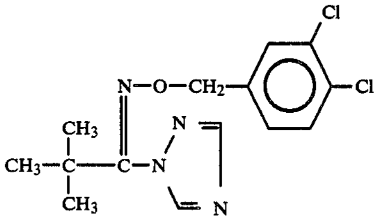

or a physiologically acceptable addition product thereof with an acid or metal salt.

8. A fungicidal composition comprising a fungicidally effective amount of a compound or addition product according to claim 1 in admixture with a diluent.

9. A method of combating fungi which comprises administering to such fungi or to a fungus habitat a fungicidally effective amount of a compound or addition product according to claim 1.

10. The method according to claim 9, wherein such compound is
2,2-dimethyl-2-methoxy-1-(4-chlorobenzyloximino)-1-(imidazol-1-yl)-ethane,
2,2-dimethyl-1-(2,6-dichlorobenzyloximino)-1-(1,2,4-triazol-1-yl)-propane,
2,2-dimethyl-1-(4-chlorobenzyloximino)-1-(imidazol-1-yl)-propane
2,2-dimethyl-2-methoxy-1-(2-chlorobenzyloximino)-1-(imidazol-1-yl)-ethane or
2,2-dimethyl-1-(3,4-dichlorobenzyloximino)-1-(1,2,4-triazol-1-yl)-propane,
or an addition product thereof with an acid or metal salt.

* * * * *